US007518015B2

(12) United States Patent
Cremer et al.

(10) Patent No.: US 7,518,015 B2
(45) Date of Patent: Apr. 14, 2009

(54) PROCESS FOR HETEROGENEOUSLY CATALYZED GAS PHASE PARTIAL OXIDATION OF AT LEAST ONE ORGANIC STARTING COMPOUND

(75) Inventors: Ulrich Cremer, Mannheim (DE); Ulrike Wegerle, Worms (DE); Gerhard Laqua, Mutterstadt (DE); Ulrich Hammon, Mannheim (DE); Klaus Joachim Mueller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/612,824

(22) Filed: Dec. 19, 2006

(65) Prior Publication Data

US 2007/0155988 A1 Jul. 5, 2007

Related U.S. Application Data

(60) Provisional application No. 60/756,207, filed on Jan. 5, 2006.

(30) Foreign Application Priority Data

Jan. 5, 2006 (DE) .................. 10 2006 000 996

(51) Int. Cl.
C07C 51/16 (2006.01)
(52) U.S. Cl. .................................. 562/532
(58) Field of Classification Search ........... 562/432, 562/532
See application file for complete search history.

(56) References Cited

U.S. PATENT DOCUMENTS

| | | | |
|---|---|---|---|
| 3,119,837 A | 1/1964 | Kingsley et al. | |
| 3,702,259 A | 11/1972 | Nielsen | |
| 3,956,377 A | 5/1976 | Dolhyj et al. | |
| 4,077,912 A | 3/1978 | Dolhyj et al. | |
| 4,408,079 A | 10/1983 | Merger et al. | |
| 4,496,770 A | 1/1985 | Duembgen et al. | |
| 5,153,162 A | 10/1992 | Kurimoto et al. | |
| 5,173,468 A | 12/1992 | Boehning et al. | |
| 5,221,767 A | 6/1993 | Boehning et al. | |
| 5,231,226 A | 7/1993 | Hammon et al. | |
| 5,264,625 A | 11/1993 | Hammon et al. | |
| 5,668,077 A | 9/1997 | Klopries et al. | |
| 5,734,068 A | 3/1998 | Klopries et al. | |
| 5,739,391 A * | 4/1998 | Ruppel et al. | 562/532 |
| 5,821,390 A | 10/1998 | Ruppel et al. | |
| 6,252,122 B1 | 6/2001 | Tenten et al. | |
| 6,395,936 B1 | 5/2002 | Arnold et al. | |
| 6,403,829 B1 | 6/2002 | Unverricht et al. | |
| 6,410,785 B1 | 6/2002 | Zehner et al. | |
| 6,781,017 B2 | 8/2004 | Machhammer et al. | |
| 6,794,539 B2 | 9/2004 | Unverricht et al. | |
| 6,858,754 B2 | 2/2005 | Borgmeier | |
| 6,867,328 B2 | 3/2005 | Borgmeier et al. | |
| 6,881,702 B2 | 4/2005 | Arnold et al. | |
| 6,933,407 B2 | 8/2005 | Berndt et al. | |
| 7,005,403 B2 | 2/2006 | Borgmeier et al. | |
| 7,026,506 B2 | 4/2006 | Borgmeier et al. | |
| 7,115,776 B2 * | 10/2006 | Hammon et al. | 562/547 |
| 7,154,009 B2 | 12/2006 | Dieterle et al. | |
| 7,176,335 B2 | 2/2007 | Berndt et al. | |
| 7,211,692 B2 | 5/2007 | Dieterle et al. | |
| 7,214,822 B2 | 5/2007 | Borgmeier et al. | |
| 7,271,279 B2 | 9/2007 | Borgmeier et al. | |
| 2003/0017095 A1 * | 1/2003 | Olbert et al. | 422/196 |
| 2003/0181762 A1 | 9/2003 | Machhammer et al. | |
| 2003/0187298 A1 | 10/2003 | Borgmeier et al. | |
| 2003/0187299 A1 | 10/2003 | Machhammer et al. | |
| 2004/0082810 A1 | 4/2004 | Borgmeier et al. | |
| 2004/0102648 A1 | 5/2004 | Borgmeier et al. | |
| 2004/0138500 A1 | 7/2004 | Borgmeier | |
| 2004/0171887 A1 | 9/2004 | Berndt et al. | |
| 2004/0181083 A1 | 9/2004 | Proll et al. | |
| 2004/0199000 A1 | 10/2004 | Borgmeier et al. | |
| 2004/0242925 A1 | 12/2004 | Berndt et al. | |
| 2005/0096483 A1 | 5/2005 | Dieterle et al. | |
| 2005/0119515 A1 | 6/2005 | Machhammer et al. | |
| 2005/0261517 A1 | 11/2005 | Dieterle et al. | |
| 2006/0074258 A1 | 4/2006 | Borgmeier et al. | |

FOREIGN PATENT DOCUMENTS

| | | |
|---|---|---|
| DE | 1 254 137 | 11/1967 |
| DE | 2 025 430 | 12/1971 |
| DE | 2 159 346 | 6/1972 |
| DE | 2 351 151 | 4/1974 |
| DE | 25 26 238 A1 | 1/1976 |
| DE | 40 22 212 A1 | 1/1992 |
| DE | 41 32 263 A1 | 4/1993 |
| DE | 41 32 684 A1 | 4/1993 |

(Continued)

OTHER PUBLICATIONS

Prof. Dr. Hans Beyer, "Lehrbuch der Organischen Chemie", vol. 17, 1973, p. 261.

*Primary Examiner*—Jafar Parsa
(74) *Attorney, Agent, or Firm*—Oblon, Spivak, McClelland, Maier & Neustadt, P.C.

(57) ABSTRACT

A process for heterogeneously catalyzed gas phase partial oxidation of an organic starting compound over a fixed catalyst bed freshly installed into a reaction chamber, in which the reduction in the quality of the fixed catalyst bed is restored with increasing operating time by replacing a portion of the fixed catalyst bed by a replacement fixed catalyst bed part whose volume-specific activity is lower than the volume-specific activity of the replaced fixed catalyst bed part in its freshly installed state.

10 Claims, No Drawings

FOREIGN PATENT DOCUMENTS

| | | |
|---|---|---|
| DE | 43 11 608 A1 | 12/1994 |
| DE | 44 31 957 A1 | 3/1995 |
| DE | 196 22 331 A1 | 12/1997 |
| DE | 199 02 562 A1 | 7/2000 |
| DE | 199 10 506 A1 | 9/2000 |
| DE | 199 10 508 A1 | 9/2000 |
| DE | 100 28 582 A1 | 12/2001 |
| DE | 100 46 672 A1 | 3/2002 |
| DE | 100 46 928 A1 | 4/2002 |
| DE | 100 46 957 A1 | 4/2002 |
| DE | 101 21 592 A1 | 5/2002 |
| DE | 10232748 | 7/2002 |
| DE | 101 31 297 A1 | 1/2003 |
| DE | 10 2004 025 445 A1 | 2/2005 |
| DE | 103 50 812 A1 | 6/2005 |
| DE | 103 50 822 A1 | 6/2005 |
| DE | 103 51 269 A1 | 6/2005 |
| EP | 0 058 927 A1 | 9/1982 |
| EP | 0 092 097 A1 | 10/1983 |
| EP | 0 253 409 A2 | 1/1988 |
| EP | 0 372 972 A1 | 6/1990 |
| EP | 0 415 347 A2 | 3/1991 |
| EP | 0 471 853 A1 | 2/1992 |
| EP | 0 522 871 A1 | 1/1993 |
| EP | 0 529 853 A2 | 3/1993 |
| EP | 0 608 838 A2 | 8/1994 |
| EP | 0 614 872 A1 | 9/1994 |
| EP | 0 700 714 A1 | 3/1996 |
| EP | 0 700 893 A1 | 3/1996 |
| EP | 0 990 636 A1 | 4/2000 |
| EP | 1 090 684 A1 | 4/2001 |
| EP | 1 097 745 A1 | 5/2001 |
| EP | 1 106 598 A2 | 6/2001 |
| EP | 1 180 508 A1 | 2/2002 |
| GB | 1 291 354 | 10/1972 |
| GB | 1 346 943 | 2/1974 |
| GB | 1 464 198 | 2/1977 |
| WO | WO 89/07101 | 8/1989 |
| WO | WO 01/96270 A2 | 12/2001 |
| WO | WO 2004/009525 A1 | 1/2004 |
| WO | WO 2005/113127 A1 | 12/2005 |

* cited by examiner

PROCESS FOR HETEROGENEOUSLY CATALYZED GAS PHASE PARTIAL OXIDATION OF AT LEAST ONE ORGANIC STARTING COMPOUND

The present invention relates to a process for heterogeneously catalyzed gas phase partial oxidation of at least one organic starting compound with molecular oxygen over a fixed catalyst bed freshly installed into a reaction chamber, in which, for the purpose of the partial oxidation, a reaction gas mixture comprising the at least one organic starting compound and the molecular oxygen is conducted through the fixed catalyst bed and heat of reaction is removed by indirect heat exchange with a fluid heat carrier conducted outside the reaction chamber, and, when increasing operating time is accompanied by an increasing reduction in the quality of the fixed catalyst bed, the quality of the fixed catalyst bed is recovered by replacing not the entire fixed catalyst bed but only a portion thereof by a replacement fixed catalyst bed part.

A full oxidation of an organic compound with molecular oxygen is understood here to mean that the organic compound is converted under the reactive action of molecular oxygen such that all of the carbon present in the organic compound is converted to oxides of carbon and all of the hydrogen present in the organic compound is converted to oxides of hydrogen. All different conversions of an organic compound under the reactive action of molecular oxygen are summarized here as partial oxidations of an organic compound.

In particular, partial oxidations shall be understood here to mean those conversions of organic compounds under the reactive action of molecular oxygen in which the organic compound to be oxidized partially, after the reaction has ended, comprises at least one oxygen atom more in chemically bonded form than before the partial oxidation was carried out.

Diluent gases which behave substantially inertly under the conditions of the heterogeneously catalyzed gas phase partial oxidation are understood to mean those diluent gases whose constituents, under the conditions of the heterogeneously catalyzed gas phase partial oxidation, each constituent alone, remain unchanged to an extent of more than 95 mol %, preferably to an extent of more than 99 mol %.

The loading of a fixed catalyst bed catalyzing a reaction step with reaction gas mixture is understood to mean the amount of reaction gas mixture in standard liters (=l(STP); the volume in liters that the corresponding amount of reaction gas mixture would take up under standard conditions, i.e. at 25° C. and 1 atm) which is fed per hour to the fixed catalyst bed based on the volume of its bed (pure inert material sections are not counted) (→unit=l(STP)/l·h). The loading may also be based only on one constituent of the reaction gas mixture. In that case, it is the volume of this constituent which is fed per hour to the fixed catalyst bed based on the volume of its bed.

It is common knowledge that partial and heterogeneously catalyzed oxidation of a wide variety of organic starting compounds with molecular oxygen in the gas phase in a fixed catalyst bed allows numerous commodity chemicals (target products) to be obtained. Examples include the conversion of propylene to acrolein and/or acrylic acid (cf., for example, DE-A 23 51 151), the conversion of tert-butanol, isobutene, isobutane, isobutyraldehyde or the methyl ether of tert-butanol to methacrolein and/or methacrylic acid (cf., for example, DE-A 25 26 238, EP-A 092 097, EP-A 058 927, DE-A 41 32 263, DE-A 41 32 684 and DE-A 40 22 212), the conversion of acrolein to acrylic acid, the conversion of methacrolein to methacrylic acid (cf., for example, DE-A 25 26 238), the conversion of o-xylene, p-xylene or naphthalene to phthalic anhydride (cf., for example, EP-A 522 871) or the corresponding acids, and also the conversion of butadiene to maleic anhydride (cf., for example, GB-A 1 464 198 and GB-A 1 291 354), the conversion of indanes to, for example, anthraquinone (cf., for example, DE-A 20 25 430), the conversion of ethylene to ethylene oxide or of propylene to propylene oxide (cf., for example, DE-B 12 54 137, DE-A 21 59 346, EP-A 372 972, WO 89/07101, DE-A 43 11 608 and Beyer, Lehrbuch der organischen Chemie [Textbook of organic chemistry], 17th edition (1973), Hirzel Verlag Stuttgart, page 261), the conversion of propylene and/or acrolein to acrylonitrile (cf., for example, DE-A 23 51 151), the conversion of isobutene and/or methacrolein to methacrylonitrile (i.e., in this document, the term partial oxidation is also intended to comprise partial ammoxidation, i.e. a partial oxidation in the presence of ammonia), the oxidative dehydrogenation of hydrocarbons (cf., for example, DE-A 23 51 151), the conversion of propane to acrylonitrile or to acrolein and/or acrylic acid (cf., for example, DE-A 101 31 297, EP-A 1 090 684, EP-A 608 838, DE-A 100 46 672, EP-A 529 853, WO 01/96270 and DE-A 100 28 582), the conversion of isobutane to methacrolein and/or methacrylic acid, and the reactions of ethane to give acetic acid, of ethylene to give ethylene oxide, of benzene to give phenol and of 1butene or 2-butene to give the corresponding butanediols, etc.

The fixed catalyst bed has the task of inducing the desired gas phase partial oxidation to proceed preferentially over full oxidation.

The chemical reaction proceeds when the reaction gas mixture flows through the fixed bed during the residence time of the reaction gas mixture therein.

The solid-state catalysts are frequently oxide compositions or noble metals (e.g. Ag). In addition to oxygen, the catalytically active oxide composition may comprise only one other element or more than one other element (in the case of so-called multielement oxide compositions).

Frequently, the catalytically active oxide compositions used are those which comprise more than one metallic element, especially transition metal. In this case, reference is made to multimetal oxide compositions. Typically, these are not simple physical mixtures of oxides of their elemental constituents, but rather mixtures of complex poly compounds of these elements. In practice, the aforementioned catalytically active solid compositions are generally used shaped to a wide variety of different geometries (rings, solid cylinders, spheres, etc.). The shaping (to the shaped body) can be effected in such a way that the catalytically active composition is shaped as such (for example in extruders or tableting apparatus), so that the result is a so-called unsupported catalyst, or by applying the active composition to a preshaped support (cf., for example, WO 2004/009525 and WO 2005/113127).

Examples of catalysts which are suitable for inventive heterogeneously catalyzed fixed bed gas phase partial oxidations of at least one organic starting compound can be found, for example, in DE-A 100 46 957, in EP-A 1 097 745, in DE-A 44 31 957, in DE-A 100 46 928, in DE-A 199 10 506, in DE-A 196 22 331, in DE-A 101 21 592, in EP-A 700 714, in DE-A 199 10 508, in EP-A 415 347, in EP-A 471 853 and in EP-A 700 893.

Typically, heterogeneously catalyzed gas phase partial oxidations proceed highly exothermically. Owing to a multitude of possible parallel and/or subsequent reactions, the sole measure of catalyst use is normally insufficient with regard to a highly selective conversion of the at least one organic starting compound to be oxidized partially to the desired target product. Instead, it is additionally required for a highly selective performance of a heterogeneously catalyzed gas phase partial oxidation in a fixed catalyst bed to control the profile of the reaction temperature or the profile of the temperature of the fixed catalyst bed in flow direction of the reaction gas mixture to a certain extent. For reasons of heat removal, such partial oxidations are therefore generally carried out in "isothermal" fixed bed reactors in which the fixed catalyst bed is disposed installed into a reaction chamber, around which a fluid heat carrier (a heat exchange medium) which touches the material shell of the reaction chamber (the wall of the reaction chamber) (is in contact with it) is conducted outside the reaction chamber for the purpose of indirect heat exchange. For example, the fixed catalyst bed may be disposed in the catalyst tubes of a tube bundle reactor, around which a salt melt or a metal melt is conducted (passed) for heat removal.

In addition, the reactants are typically diluted with a gas which is substantially inert under the conditions of the heterogeneously catalyzed gas phase partial oxidation and is capable of absorbing heat of reaction released with its heat capacity.

The reaction gas mixture of a heterogeneously catalyzed gas phase partial oxidation of at least one organic starting compound will therefore, in addition to the at least one organic starting compound and molecular oxygen, generally additionally comprise at least one inert diluent gas.

One of the most frequently used inert diluent gases is molecular nitrogen which is automatically used whenever the oxygen source used for the heterogeneously catalyzed gas phase partial oxidation is air.

Another inert diluent gas used in many cases is steam owing to its general availability.

Other typically used inert diluent gases are noble gases (e.g. He, Ar, Ne) or the carbon oxides $CO_2$ and/or CO.

The use of diluent gases with maximum molar heat capacity is usually particularly advantageous (cf., for example, EP-A 253 409). For example, in the case of a partial oxidation of an unsaturated organic starting compound, these frequently include saturated hydrocarbons, for example propane in the case of a partial oxidation of propylene to acrolein and/or acrylic acid.

In many cases, cycle gas is also used as an inert diluent gas (cf., for example, EP-A 1 180 508). Cycle gas refers to the residual gas which remains after a one-stage or multistage (in the multistage heterogeneously catalyzed gas phase partial oxidation of at least one organic starting compound, the gas phase partial oxidation, in contrast to the one-stage heterogeneously catalyzed gas phase partial oxidation, is carried out not in one, but rather in at least two reactor sections (reaction chambers) connected in series (which can merge into one another seamlessly in a common casing or be accommodated in two spatially separate reactors connected in series), in which case, if appropriate, inert gas and/or oxidant are supplemented between successive reactor sections or reactors; multiple stages are employed especially when the partial oxidation proceeds in successive steps; in these cases, it is frequently appropriate to optimize both the fixed catalyst bed and the other reaction conditions to the particular reaction step, and to carry out the reaction step in a dedicated reactor section or in a dedicated reactor, i.e. as a or in a separate reaction stage; however, it can also be employed when, for reasons of heat removal or for other reasons (cf., for example, DE-A 199 02 562), the conversion is spread over a plurality of reactor sections or reactors connected in series; an example of a heterogeneously catalyzed gas phase partial oxidation frequently carried out in two stages is the partial oxidation of propylene to acrylic acid; in the first reaction stage, the propylene is partially oxidized to acrolein and, in the second reaction stage, the acrolein to acrylic acid; methacrylic acid preparation, usually starting from isobutene, is also frequently carried out in two stages in a corresponding manner; however, both aforementioned partial oxidations may also be carried out in one stage (both steps in one reactor section over a fixed catalyst bed with catalyst catalyzing both steps) when suitable catalyst charges are used, as described, for example, in DE-A 101 21 592 for the partial oxidation of propylene to acrylic acid) heterogeneously catalyzed gas phase partial oxidation of at least one organic compound when the target product has been removed more or less selectively (for example by absorption into a suitable solvent or by fractional condensation) from the product gas mixture. In general, it consists predominantly of the inert diluent gases used for the partial oxidation, and also of steam typically formed as a by-product in the partial oxidation or added as a diluent gas and carbon oxides formed by undesired full oxidation. In some cases, it also comprises small amounts of molecular oxygen unconsumed in the partial oxidation (residual oxygen) and/or of unconverted organic starting compound.

However, the inert diluent gases used are not only helpful in absorbing the heat of reaction but also generally simultaneously ensure safe operation of the heterogeneously catalyzed gas phase partial oxidation of the at least one organic starting compound by keeping the reaction gas mixture either outside the explosion range or within a region of the explosion range which is still safely controllable.

In spite of the external and internal measures described for controlling (regulating) the reaction temperature or the temperature of the fixed catalyst bed, it is necessary to distinguish between the "temperature of the fixed catalyst bed" and the "effective temperature of the fixed catalyst bed" owing to the difference between them which normally exists in spite of these measures.

The temperature of the fixed catalyst bed is understood to mean the temperature of the fixed catalyst bed when the partial oxidation process is performed, but in the theoretical absence of a chemical reaction (i.e. without the influence of the heat of reaction) (i.e. the influence of the fluid heat carrier conducted outside the reaction chamber is included in the same way as when the partial oxidation process is performed). In contrast, effective temperature of the fixed catalyst bed is understood to mean the actual temperature of the fixed catalyst bed with additional inclusion of the partial oxidation. When the temperature of the fixed catalyst bed is not constant along the fixed catalyst bed (for example in the case of a plurality of temperature zones), the term temperature of the fixed catalyst bed in this document means the (numerical) mean of the temperature along the fixed catalyst bed. However, the process according to the invention is especially suitable when the temperature of the fixed catalyst bed is constant along the fixed catalyst bed in flow direction of the reaction gas mixture.

It is of significance in the aforementioned context that the temperature of the reaction gas mixture (and hence also the effective temperature of the fixed catalyst bed) as it passes through the fixed catalyst bed in flow direction of the reaction gas mixture in the particular reaction stage typically passes through a maximum value (the so-called hot-spot value). The difference between hotspot value and the temperature of the fixed catalyst bed at the position of the hotspot value is referred to as the hotspot expansion $\Delta T^{HB}$. This is attributable, inter alia, to the reactant concentration in the reaction gas mixture being at a maximum at the inlet (entrance) of the reaction gas mixture into the fixed catalyst bed, which causes particularly high reaction rates there, which are accompanied by particularly high evolution of heat of reaction per unit time (on entry into the fixed catalyst bed, the reaction gas mixture generally has substantially the temperature of the fixed catalyst bed).

Usually, heterogeneously catalyzed gas phase partial oxidations require elevated fixed catalyst bed temperatures for economically viable reactant conversions of the partial oxidation based on single pass of the reaction gas mixture through the fixed catalyst bed. In general, these are a few hundred ° C., typically from 100 to 600° C., frequently from 150 to 500° C., usually from 200 or 250 to 450° C.

The working pressure in heterogeneously catalyzed gas phase partial oxidations over a fixed catalyst bed may be below 1 atm or above 1 atm. In general, it is in the range from $\geq 1$ to 20, or to 10 atm. It is common knowledge that heterogeneously catalyzed gas phase partial oxidations of at least one organic compound over a fixed catalyst bed installed freshly into a reaction chamber can be operated substantially continuously over prolonged periods over one and the same fixed catalyst bed. In this case, the reaction conditions can generally be retained at a substantially constant level.

However, the fixed catalyst bed normally loses quality in the course of the operating time. In general, the volume-specific activity of the fixed catalyst bed in particular deteriorates (the higher the temperature of the catalyst bed required for a certain reactant conversion based on single pass of the reaction gas mixture through the fixed catalyst bed under otherwise unchanged reaction conditions, the lower the volume-specific activity of the fixed catalyst bed). Usually, the selectivity of target product formation also suffers.

A decreasing volume-specific activity of a fixed catalyst bed is disadvantageous in particular because this reduces the reactant conversion based on single pass of the reaction gas mixture through the fixed catalyst bed under otherwise constant operating conditions with increasing operating time of the fixed catalyst bed, which reduces the intended space-time yield of target product in a production plant.

EP-A 990 636 and EP-A 1 106 598 attempt to take account of the aforementioned development in the long-term operation of a heterogeneously catalyzed gas phase partial oxidation of at least one organic starting compound over one and the same fixed catalyst bed by gradually increasing the temperature of the fixed catalyst bed in the course of the operating time under otherwise substantially constant operating conditions, in order to substantially retain the reactant conversion in single pass of the reaction gas mixture through the fixed catalyst bed.

In this document, the deactivation rate of a fixed catalyst bed refers to the increase in the temperature of the fixed catalyst bed which is required to retain the reactant conversion in single pass of the reaction gas mixture through the fixed catalyst bed (under otherwise unchanged process conditions) scaled up to an operating time of one year (365 days).

However, a disadvantage of the procedure recommended in EP-A 990 636 and in EP-A 1 106 598 is that, with increasing elevation of the temperature of the fixed catalyst bed, its aging process is generally accelerated, which is why, on attainment of a maximum value of the temperature of the fixed catalyst bed, the fixed catalyst bed is typically exchanged fully and a completely unused fixed catalyst bed is installed freshly into the reaction chamber (the deactivation can no longer be balanced by an increase in the temperature of the fixed catalyst bed).

DE-A 103 51 269, DE-A 103 50 812, DE-A 103 50 822, EP-A 614 872 and DE-A 103 50 822 recommend delaying the need to fully exchange the fixed catalyst bed by regenerating the fixed catalyst bed from time to time (i.e. interrupt the process for heterogeneously catalyzed fixed bed gas phase partial oxidation from time to time and, for example, conduct a hot mixture of molecular oxygen and inert gas through the fixed catalyst bed). However, a disadvantage of this procedure is that its effectiveness is exhausted with increasing overall operating time.

As a further measure to delay the need to fully exchange the fixed catalyst bed, DE-A 10 2004 025 445 recommends an increase in the working pressure in the gas phase. However, a disadvantage of this measure is that its effectiveness is likewise exhausted with increasing overall operating time and that it simultaneously requires an increasing compression output.

As a further means of delaying a full exchange of the fixed catalyst bed, DE-A 102 32 748 and WO 2004/009525 recommend replacing only a part thereof with a replacement fixed catalyst bed whose volume-specific activity should be equal to that of the replaced fixed catalyst bed part in its state freshly installed into the reaction chamber.

In this manner, it is possible to regain the required reactant conversion (based on single pass of the reaction gas mixture through the fixed catalyst bed) under otherwise unchanged process conditions with a comparatively restricted increase in temperature of the fixed catalyst bed (compared with the temperature of the fixed catalyst bed required for the same reactant conversion with the fixed catalyst bed originally installed freshly into the reaction chamber).

However, a disadvantage of the procedure described in DE-A 102 32 748 and in WO 2004/009525 is that, after the partial replacement of the fixed catalyst bed, the deactivation rate of the fixed catalyst bed resulting after the partial replacement, in the course of operation thereof at temperatures which ensure the required reactant conversion, is increased (compared with the deactivation rate of the fixed catalyst bed installed freshly into the reaction chamber with an otherwise corresponding operating mode aimed at the same reactant conversion), which is why the time span available after the partial replacement until the need for a full exchange of the fixed catalyst bed is comparatively restricted.

It was therefore an object of the present invention to provide an improved embodiment of a partial replacement of a spent fixed catalyst bed, which is accompanied by a lower deactivation rate of the fixed catalyst bed resulting after the partial replacement in an operating mode which is aimed at the same reactant conversion and also corresponds otherwise than is the case for a partial replacement according to DE-A 102 32 748 and WO 2004/009525.

Accordingly, a process has been found for heterogeneously catalyzed gas phase partial oxidation of at least one organic starting compound with molecular oxygen over a fixed catalyst bed freshly installed into a reaction chamber, in which, for the purpose of the partial oxidation, a reaction gas mixture comprising the at least one organic starting compound and the molecular oxygen is conducted through the fixed catalyst bed and heat of reaction is removed by indirect heat exchange with a fluid heat carrier conducted outside the reaction chamber, and, when increasing operating time is accompanied by an increasing reduction in the quality of the fixed catalyst bed, not the entire fixed catalyst bed but only a portion thereof is replaced by a replacement fixed catalyst bed part (with generally freshly prepared catalyst), wherein the volume-specific activity of the replacement fixed catalyst bed part is lower than the volume-specific activity of the replaced fixed catalyst bed part in its freshly installed state.

As already mentioned, the measure employed for the volume-specific activity of a fixed catalyst bed charge (or such a section), with identical bed volume, is the temperature of the fixed catalyst bed charge which is required to achieve the reactant conversion desired (in industrial scale production) based on single pass of the reaction gas mixture through the fixed catalyst bed charge under otherwise identical process conditions (identical composition of the reaction gas mixture, identical loading of the fixed catalyst bed charge with reaction gas mixture). The higher the temperature required, the lower the volume-specific activity. Alternatively, at identical temperature of the fixed catalyst bed charge and identical other process conditions or operating conditions (identical composition of the reaction gas mixture, identical loading of the fixed catalyst bed charge with reaction gas mixture), it is possible to employ the resulting reactant conversion based on single pass through the fixed catalyst bed. The higher the reactant conversion achieved, the higher the volume-specific activity.

The volume-specific (i.e. normalized to the unit of bed volume) activity can be reduced in a simple manner, for example, by homogeneously diluting a basic amount of uniformly produced shaped catalyst bodies with inert shaped diluent bodies. The higher the selected fraction of inert shaped diluent bodies, the lower the amount of active composition and catalyst activity present in a certain volume of the bed. Inert shaped diluent bodies are understood to mean shaped bodies of those materials which behave substantially inertly with regard to the heterogeneously catalyzed partial gas phase oxidation, i.e. as far as possible cause substantially no reactant conversion. Useful such materials for the majority of the heterogeneously catalyzed gas phase partial oxidations of organic starting compounds are, for example, porous or nonporous aluminum oxides, silicon dioxide, thorium dioxide, zirconium dioxide, silicon carbide, silicates such as magnesium silicate or aluminum silicate, or steatite.

The geometry of such inert shaped diluent bodies may in principle be as desired. In other words, they may, for example, be spheres, polygons, solid cylinders or rings. Preferably in accordance with the invention, the inert shaped diluent bodies selected will be those whose geometry corresponds to that of the shaped catalyst bodies to be diluted with them. However, a decrease in the volume-specific activity is also possible, for example, by, with uniform geometry and active composition type of a coated shaped catalyst body, reducing the thickness of the active composition layer applied to the support or, in a mixture of coated catalysts with the same geometry but with different proportion by weight of the active composition, increasing the proportion of shaped catalyst bodies with lower proportion by weight of active composition. A similar effect can also be achieved, for example, by changing the mixing ratio appropriately in mixtures of unsupported catalysts and of coated catalysts (with identical active composition). Of course, the variants described can also be employed in combination. However, the volume-specific activity can also be reduced by, with the same elemental composition of the active composition and with the same shaping process, reducing the specific surface area of the active composition, for example, by thermally treating the active composition at elevated temperature and/or over a prolonged period.

It will be appreciated that the volume-specific activity can also be influenced by, for example, with identical shaping, changing the elemental composition of the active composition and, for example, reducing the proportion of those elemental constituents which are particularly beneficial for increased activity. Alternatively, it is also possible to dilute the active compositions themselves by, in the active composition preparation, for example, incorporating inert diluting materials such as hard-fired silicon dioxide into the dry mixture of starting compounds to be treated thermally. Different added amounts of diluting material lead automatically to different activities. The more diluting material is added, the lower the resulting activity will be. All aforementioned measures, each alone or in any combination, are useful for controlling the volume-specific activity of the replacement fixed catalyst bed part in the inventive sense. This includes not least also the possibility of increasing the longest dimension of the support body (for example the diameter of the support sphere) with the same geometric shape of a coated catalyst and the same coating thickness and same active composition coating.

The background to the inventive teaching is the fact that a fixed catalyst bed freshly installed in a reaction chamber loses its quality over the fixed catalyst bed in a nonhomogeneous, nonuniform manner in the course of the operating time of a heterogeneously catalyzed gas phase partial oxidation of at least one organic starting compound carried out over it (cf., for example, WO 2004/009525). The cause of this may, for example, be hotspot formation and/or the inhomogeneous enrichment of catalyst poisons present in the reaction gas mixture (the industrial scale reaction gas mixtures start from raw materials which are not highly pure). Irrespective of the specific cause, the higher the effective temperature of the fixed catalyst bed in the fixed catalyst bed section in question, though, the more rapidly the deactivation in the particular fixed catalyst bed section proceeds.

When, after a prolonged operating time, such a disproportionately deactivated section of the fixed catalyst bed is then replaced by a replacement fixed catalyst bed part whose volume-specific activity corresponds to the volume-specific activity of the replaced fixed catalyst bed section in its freshly installed state, the overall fixed catalyst bed then consists of two subsections. One is in the fresh original state, the other in a state deactivated subproportionally by preceding operation. In order to achieve the same reactant conversion as in a complete fixed catalyst bed installed freshly into the reaction chamber under otherwise unchanged operating conditions with such a fixed catalyst bed, based on single pass of the reaction gas mixture, a higher fixed catalyst bed temperature is required in the former case than in the latter case. However, this causes a disproportionately increased effective fixed catalyst bed temperature in the fresh replacement fixed catalyst bed part, since the activity of a fresh catalyst bed charge grows in a greater than linear manner within increasing operating temperature (cf. EP-A 099 636 and EP-A 1 106 598). An even lower proportion of conversion than prior to the partial catalyst bed change is accounted for by the unexchanged fixed catalyst bed section. Together, this causes a higher deactivation rate than in the case of operation of the fixed catalyst bed installed freshly in its entirety into the reaction chamber.

When the replacement fixed catalyst bed part, in contrast, has a lower volume-specific activity than the replaced fixed catalyst bed section in its freshly installed state, it does require an even higher fixed catalyst bed temperature to obtain the desired reactant conversion, but the unexchanged fixed catalyst bed section in this case has to contribute a comparatively increased proportion of conversion (of course, the above considerations always assume retention of the composition of the reaction gas mixture and of the loading of the fixed catalyst bed with reaction gas mixture). This is generally accompanied by lower hotspot expansions $\Delta T^{HB}$ and the ultimate result is normally lower deactivation rates than in the case of a replacement fixed catalyst bed part with a volume-specific activity which corresponds to that in the originally freshly installed state.

However, the consequence of such a comparatively reduced deactivation rate is normally an increased overall operating time until a complete exchange of the fixed catalyst bed is required. In other words, the attraction of the process according to the invention consists in very substantially activating the catalytic potential of the unexchanged, previously under-utilized section of the fixed catalyst bed and accessing it subsequently. This procedure explicitly and astonishingly includes partial fixed catalyst bed changes in which the volume-specific activity of the replacement fixed catalyst bed part is lower than the volume-specific activity of the replaced fixed catalyst bed part at the time of its replacement. However, the shaped catalyst bodies in the replacement fixed catalyst bed part normally are or comprise freshly prepared shaped catalyst bodies. The reason for a further economic advantage of the inventive procedure over the prior art procedure is that a lower volume-specific activity of the replacement fixed catalyst bed part is accompanied, for example, by an increased proportion of inert shaped diluent bodies, which reduces the financial expenditure for the replacement fixed catalyst bed part. Instead of exercising the economic advantage of a lower deactivation rate, it is of course alternatively also possible to increase the loading of the fixed catalyst bed with reaction gas mixture and thus, for example, to increase the space-time yield of target product while retaining the previous deactivation rate. Advantageously in accordance with the invention, the volume-specific activity of the replacement fixed catalyst bed part will be such that, based on the same reactant conversion in single pass of the reaction gas mixture through the fixed catalyst bed and the same reaction gas mixture composition and loading of the fixed catalyst bed with reaction gas mixture, the difference d$\Delta$T between the hotspot expansion $\Delta T^{HB}_{n}$ after the partial change of the fixed catalyst bed and the hotspot expansion $\Delta T^{HB}_{v}$ (immediately) before the partial change of the fixed catalyst bed (d$\Delta$T=$\Delta T^{HB}_{n}$-$\Delta T^{HB}_{v}$) is $\leq$30° C. The volume-specific activity of the replacement fixed catalyst bed part is preferably such that d$\Delta$T is $\leq$25° C., or $\leq$20° C. or $\leq$15° C., better $\leq$10 or $\leq$5° C., more advantageously $\leq$0° C., or $\leq$-5° C., or $\leq$-10° C., in many cases $\leq$-15° C. or up to -20° C. In general, d$\Delta$T will not be $\leq$-20° C. Preference is given to processes according to the invention in which d$\Delta$T is from -15 to +10° C. Particular preference is given to those processes according to the invention in which d$\Delta$T is from -10° C. to 0° C. Also favorable is a d$\Delta$T of from -5° C. to 0° C.

By way of example, the reaction chamber of the process according to the invention may be the interior of a (catalyst or reaction) tube in which the fixed catalyst bed is installed and around whose exterior the fluid heat carrier is conducted. This can in principle be conducted in cocurrent, in countercurrent or in cross current to the reaction gas mixture conducted through the reaction tube. Appropriately, the catalyst tube is disposed in a tube bundle reactor.

In other words, appropriately in accordance with the invention, the inventive heterogeneously catalyzed gas phase partial oxidation of the at least one organic starting compound will be carried out on the industrial scale in a multiple catalyst tube fixed bed reactor (tube bundle reactor). Such reactors are of a corresponding type to shell-and-tube heat exchangers (in principle, though, any other type of known indirect heat exchangers is useful for accommodating the fixed catalyst bed for the process according to the invention). In other words, their customary design consists of a generally cylindrical vessel in which a multitude of (normally identical) (reaction) tubes corresponding to the cooling tubes of a shell-and-tube heat exchanger is accommodated in typically vertical arrangement. These catalyst tubes, of which each comprises a (normally very substantially identical) bed of the fixed catalyst bed to be used (a fixed bed arrangement of the corresponding catalyst charge), are secured with sealing by their ends typically into tube plates and appropriately open into a hood bonded to the vessel at the upper and at the lower end. Through these hoods, the reaction gas mixture flowing through the catalyst tubes is fed and removed, so that the interior of each catalyst tube corresponds to a longitudinally extended inventive (very substantially uniform) reaction chamber.

The fluid heat carrier (the fluid heat exchange medium) is conducted through the space surrounding the catalyst tubes, in order to remove (to manage) the heat of reaction (the process heat). After leaving the vessel, the heated fluid heat carrier is brought back to its original temperature before it is fed back to the reaction vessel (cf., for example, DE-A 30 42 468).

When heat carrier (heat exchange medium) enters the reactor at different (several) heights along the catalyst tubes (reaction tubes), reference will be made in this document to use of a plurality of heat exchange medium circuits or else to a multizone reactor (reaction chamber) having a plurality of temperature zones (the individual circuits are generally substantially separated from one another by suitable separating sheets). When the heat carrier (the heat exchange medium) enters only at one height (for these cases, preference is given to the process according to the invention), reference is made here to one heat exchange medium circuit or else to a one-zone reactor, even when this circuit is operated not with one pump, but with a plurality of pumps for reasons of convenience.

In other words, the process according to the invention comprises, as one embodiment, especially processes for heterogeneously catalyzed gas phase partial oxidation of at least one organic starting compound with molecular oxygen over a fixed catalyst bed installed freshly into the reaction chambers (into the catalyst tubes) of a multiple catalyst tube fixed bed reactor, in which, for the purpose of the partial oxidation, a reaction gas mixture comprising the at least one organic starting compound and the molecular oxygen is conducted through the fixed catalyst bed and heat of reaction is removed by indirect heat exchange with a fluid heat carrier conducted outside the reaction chambers (catalyst tubes), and, when increasing operating time is accompanied by an increasing reduction in the quality of the fixed catalyst bed, the quality of the fixed catalyst bed is recovered by replacing not the entire fixed catalyst bed but only a portion thereof by a replacement fixed catalyst bed part in the respective catalyst tube, wherein the volume-specific activity of the replacement fixed catalyst bed part is lower than the volume-specific activity of the replaced fixed catalyst bed part in its freshly installed state. This is especially true when heat carrier is conducted into the reactor only at one height along the catalyst tubes and it is thus a one-zone reactor. All statements made about the process according to the invention in this document relate especially to these two embodiments, especially the quantifications of d$\Delta$T.

Examples of one-zone and multizone multiple catalyst tube fixed bed reactors usable in accordance with the invention can be found, for example, in the documents DE-A 100 24 348, DE-A 198 36 792, DE-A 100 32 304, WO 01/87476, DE-A 199 10 508, DE-A 199 10 506, DE-A 199 27 624, DE-A 199 48 241, DE-A 199 48 248, DE-A 199 48 523, DE-A 199 55 168, DE-A 101 34 026, DE-A 101 34 026, DE-A 101 01 695, U.S. Pat. No. 5,442,108, EP-A 911 313, EP-A 1 097 745, DE-A 101 37 768, DE-A 101 35 498 and DE-A 100 40 781.

Typically, the catalyst tubes are manufactured from ferritic steel and frequently have a wall thickness of from 1 to 3 mm.

Their internal diameter is in many cases from 20 to 30 mm, frequently from 21 to 26 mm. Normally, the tube length extends to a few meters (a typical catalyst tube length is in the range from 2 to 4 m, frequently from 2.5 to 3.5 m). Of this, generally at least 60%, frequently at least 75% is occupied by fixed catalyst bed. Appropriately in accordance with the invention, the number of catalyst tubes accommodated in the vessel amounts to at least 5000, preferably to at least 10000. Frequently, the number of catalyst tubes accommodated in the vessel is from 15000 to 30000, or to 40000. Tube bundle reactors having a number of catalyst tubes of above 50000 usually form the exception. Within the vessel, the catalyst tubes are normally distributed homogeneously, the distribution appropriately being selected such that the separation of the central internal axes of mutually adjacent catalyst tubes (the so-called catalyst tube pitch) is from 30 to 50 mm, frequently from 35 to 45 mm (cf., for example, EP-A 468 290).

Useful fluid heat carriers for the process according to the invention are quite generally, but especially in the case of a multiple catalyst tube fixed bed reactor, salt melts, for example the salts of potassium nitrate, potassium nitrite, sodium nitrite and/or sodium nitrate. In some cases, it is also possible, depending on their melting point, to use the melts of low-melting metals such as sodium, mercury and of alloys of different metals.

The heat exchange medium, the heat carrier may, in a simple manner, be conducted substantially directly longitudinally (in cocurrent or countercurrent to the reaction gas mixture) to the catalyst tubes. However, the possibility also exists of implementing this longitudinal flow (in cocurrent or in countercurrent to the reaction gas mixture) only viewed over the entire reactor, and to superimpose a crossflow on this longitudinal flow within the reactor by virtue of an arrangement, in succession along the catalyst tubes, of deflecting disks which leave passage cross sections free, so as to result in a meandering flow profile of the heat exchange medium in longitudinal section through the tube bundle. In general, the heat exchange medium leaves the vessel (reactor) with a temperature which (caused by the exothermicity of the reaction) is above its entrance temperature (frequently from $\geq 0$ to $10°$ C., often from $\geq 2$ to $8°$ C., in many cases from $\geq 3$ to $6°$ C.).

The above statements and all others on the process according to the invention in this document have validity especially for the heterogeneously catalyzed fixed bed gas phase partial oxidation of propylene to acrolein and/or acrylic acid, of isobutene to methacrolein and/or methacrylic acid, of (meth) acrolein to (meth)acrylic acid, of propane to acrolein and/or acrylic acid and of isobutene to methacrolein and/or methacrylic acid. Of course, they are also valid for all other partial oxidations named at the outset of this document.

It is favorable in accordance with the invention when the fixed catalyst bed installed freshly into the reaction chamber in the process according to the invention is configured in a manner advantageous in accordance with the invention such that its volume-specific activity varies in flow direction of the reaction gas mixture. With particular advantage, it will be configured such that its volume-specific activity in flow direction of the reaction gas mixture increases abruptly at least once, or in a stepwise manner or continuously.

With particular advantage, the fixed catalyst bed freshly installed into the reaction chamber does not comprise any decrease in the volume-specific activity in flow direction of the reaction gas mixture. It is also favorable in accordance with the invention when the catalysts of the fixed catalyst bed installed freshly into the reaction chamber have only one active composition which, with particular advantage, is shaped to a single shaped body geometry used in this fixed catalyst bed. In addition, it is favorable in accordance with the invention when this aforementioned catalyst type in its freshly prepared form is also used as the sole catalyst for the replacement fixed catalyst bed part.

It is also favorable in accordance with the invention when only one type of inert shaped diluent body is used additionally within the fixed catalyst bed installed freshly into the reaction chamber. This shaped diluent body should then appropriately also be used for the replacement fixed catalyst bed part. The inventive procedure is thus particularly advantageous when the replacement fixed catalyst bed part and the section of the fixed catalyst bed replaced by it in its state installed freshly into the reaction chamber differ from one another only by the increased proportion of shaped diluent bodies in the replacement fixed catalyst bed part.

The inventive procedure will be described in detail below without any kind of restriction of its general validity and using the process of a heterogeneously catalyzed fixed bed gas phase partial oxidation of propylene to acrolein and/or acrylic acid merely as an example (however, these remarks are applicable correspondingly to other possible processes according to the invention for heterogeneously catalyzed fixed bed gas phase partial oxidation of other organic starting compounds and target products). All statements made in this document relate in particular to these two processes. The propylene raw material required in this regard is generally fed to the reaction gas mixture to be used as a constituent of polymer-grade or chemical-grade propylene (cf. WO 2004/ 009525). It will be appreciated that a heterogeneously catalyzed partial dehydrogenation or oxydehydrogenation of propane may also function as the propylene source, as described, for example, in WO 01/96270 and DE-A 103 16 039, WO 01/95271, DE-A 33 13 573, WO 03/011804, DE-A 102 45 585 and DE-A 10 2004 032 129 and DE-A 10 2005 013 039.

Since the heterogeneously catalyzed fixed bed gas phase partial oxidation of propylene to acrylic acid proceeds in two steps successive in time via acrolein as the intermediate compound, it can, as already mentioned, be carried out in one or two stages.

Apart from the inventive partial fixed catalyst bed change, an inventive two-stage heterogeneously catalyzed partial oxidation of propylene to acrylic acid can be carried out using a starting reaction gas mixture comprising propylene, for example as described in the documents EP-A 700 714 (first reaction stage; as described there, but also in corresponding countercurrent mode of salt bath and starting reaction gas mixture over the tube bundle reactor), EP-A 700 893 (second reaction stage; as described there but also in corresponding countercurrent method), WO 04/085369 (especially this document is considered to be an integral part of this document) (as a two-stage process), WO 04/085363, DE-A 103 13 212 (first reaction stage), EP-A 1 159 248 (as a two-stage process), EP-A 1 159 246 (second reaction stage), EP-A 1 159 247 (as a two-stage process), DE-A 199 48 248 (as a two-stage process), DE-A 101 01 695 (two-stage), WO 04/085368 (as a two-stage process), DE-A 103 51 269 (two-stage), DE-A 10 2004 021 764 (two-stage), WO 04/085362 (first reaction stage), WO 04/085370 (second reaction stage), WO 04/085365 (second reaction stage), WO 04/085367 (two-stage), WO 2004/009525 (two-stage), EP-A 990 636, EP-A 1 007 007 and EP-A 1 106 598.

This is true especially for all working examples present in these documents. When there is feeding of molecular secondary oxygen between the two reaction stages in the two-stage process, this is preferably done in the form of air. However, it can also be done in the form of pure molecular oxygen or else as another mixture of molecular oxygen and of inert gas. Advantageously, the secondary oxygen is fed in such an amount that the product gas mixture of the second reaction stage (acrolein→acrylic acid) still comprises unconverted molecular oxygen. However, the amount of molecular oxygen required for the overall process may also already be added to the reaction gas mixture for the first reaction stage (propylene→acrolein). In general, the molar ratio of molecular oxygen present in the reaction gas mixture fed to the fixed catalyst bed of the first reaction stage to propylene present therein will be $\geq 1$ and $\leq 3$.

Multimetal oxide catalysts suitable for the particular reaction stage of the two have been described many times before and are well known to those skilled in the art. For example, EP-A 253 409 on page 5 refers to appropriate US patents. Suitable catalysts for the particular oxidation stage (reaction stage) are also disclosed by DE-A 44 31 957, DE-A 10 2004 025 445 and DE-A 44 31 949. This also applies to those of the general formula I in the two aforementioned prior documents. Catalysts usable for the particular oxidation stage (reaction stage) are also disclosed by the documents DE-A 103 25 488, DE-A 103 25 487, DE-A 103 53 954, DE-A 103 44 149, DE-A 103 51 269, DE-A 103 50 812 and DE-A 103 50 822.

Useful catalysts for the first reaction stage (propylene→acrolein) are accordingly especially catalysts whose active composition is at least one multimetal oxide comprising molybdenum and/or tungsten and at least one of the elements bismuth, tellurium, antimony, tin and copper. Among these, preference is given to those whose active composition is a multimetal oxide comprising Mo, Bi and Fe.

Multimetal oxide active compositions which comprise Mo, Fe and Bi and are possible in the first reaction stage are, for example, the multimetal oxide active compositions of the general formula I of DE-A 199 55 176, the multimetal oxide active compositions of the general formula I of DE-A 199 48 523, the multimetal oxide active compositions of the general formulae I, II and III of DE-A 101 01 695, the multimetal oxide active compositions of the general formulae I, II and III of DE-A 199 48 248 and the multimetal oxide active compositions of the general formulae I, II and III of DE-A 199 55 168, and also the multimetal oxide active compositions mentioned in EP-A 7 00 714. However, all multimetal oxide compositions which comprise Mo, Bi and Fe and are mentioned in WO 2004/009525 for the first reaction stage are also useful.

Also suitable for the first reaction stage of the process according to the invention are the multimetal oxide catalysts comprising Mo, Bi and Fe which are disclosed in the documents Research Disclosure No. 497012 of Aug. 29, 2005, DE-A 100 46 957, DE-A 100 63 162, DE-C 3 338 380, DE-A 199 02 562, EP-A 15 565, DE-C 2 380 765, EP-A 8 074 65, EP-A 279 374, DE-A 330 00 44, EP-A 575 897, US-A 4 438 217, DE-A 19855913, WO 98/24746, DE-A 197 46 210 (those of the general formula 11), JP-A 91/294 239, EP-A 293 224 and EP-A 700 714. This applies in particular to the exemplary embodiments in these documents, and among these particular preference is given to those of EP-A 15 565, EP-A 575 897, DE-A 197 46 210 and DE-A 198 55 913. Particular emphasis is given in this context to a catalyst according to Example 1 c from EP-A 15 565 and also to a catalyst to be prepared in a corresponding manner but whose active composition has the composition $Mo_{12}Ni_{6.5}Zn_2Fe_2Bi_1P_{0.0065}K_{0.06}O_x \cdot 10\ SiO_2$. Emphasis is also given to the example having the serial number 3 from DE-A 198 55 913 (stoichiometry: $Mo_{12}Co_7Fe_3Bi_{0.06}K_{0.08}Si_{1.6}O_x$) as an unsupported hollow cylinder catalyst of geometry 5 mm×3 mm×2 mm (external diameter×height×internal diameter) and also to the unsupported multimetal oxide 11 catalyst according to Example 1 of DE-A 197 46 210. Mention should also be made of the multimetal oxide catalysts of U.S. Pat. No. 4,438,217. The latter is especially true when these hollow cylinders have a geometry of 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Further possible catalyst geometries in this context are extrudates (for example length 7.7 mm and diameter 7 mm; or length 6.4 mm and diameter 5.7 mm).

A multitude of the multimetal oxide active compositions which comprise Mo, Fe and Bi and are suitable for the first reaction stage can be encompassed by the general formula IV

$$Mo_{12}Bi_aFe_bX^1_cX^2_dX^3_eX^4_fO_n \qquad (IV)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a =from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in IV other than oxygen.

The above is true in particular when they are obtained in a manner known per se (see, for example, DE-A 4 023 239) and are used in accordance with the invention, for example, shaped in substance to give spheres, rings or cylinders or else in the form of coated catalysts, i.e. preshaped inert support bodies coated with the active composition. It will be appreciated that the statements made also apply when they are used in powder form as catalysts for the first reaction stage (propylene→acrolein).

In principle, active compositions of the general formula IV are prepared in a simple manner generally by obtaining a very intimate, preferably finely divided dry mixture having a composition corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature. Useful sources for the elemental constituents of the multimetal oxide active compositions IV are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture).

The starting compounds for preparing multimetal oxide active compositions IV can be intimately mixed in dry or in wet form. When they are mixed in dry form, the starting compounds are appropriately used as finely divided powders and subjected to calcination after mixing and, if appropriate, compacting. However, preference is given to intimate mixing in wet form. Typically, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The multimetal oxide active compositions of the general formula IV may be used for the first reaction stage of an inventive partial oxidation of propylene to acrylic acid either in powder form or shaped to certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Instead of graphite, it is also possible to use hexagonal boron nitride as an assistant in the shaping, as recommended by DE-A 10 2005 037 678. Examples of suitable unsupported catalyst geometries include solid cylinders or hollow cylinders having an external diameter and a length of from 2 to 10 mm. In the case of the hollow cylinder, a wall thickness of from 1 to 3 mm is advantageous. The unsupported catalyst can of course also have spherical geometry, and the spherical diameter can be from 2 to 10 mm.

A particularly favorable hollow cylinder geometry is 5 mm×3 mm×2 mm (external diameter×length×internal diameter), especially in the case of unsupported catalysts.

A pulverulent active composition suitable in accordance with the invention or its pulverulent precursor composition which is yet to be calcined and/or partially calcined may of course also be shaped by applying to preshaped inert catalyst supports. The coating of the support bodies to produce the coated catalysts is generally performed in a suitable rotatable vessel, as disclosed, for example, by DE-A 2 909 671, EP-A 293 859 or EP-A 714 700. To coat the support bodies, the powder composition to be applied is appropriately moistened and dried again after application, for example by means of hot air. The coating thickness of the powder composition applied to the support body is frequently selected within the range from 10 to 1000 µm, preferably within the range from 50 to 500 µm and more preferably within the range from 150 to 250 µm.

Useful support materials are the customary porous or nonporous aluminum oxides, silicon dioxide, thorium dioxide, zirconium dioxide, silicon carbide or silicates such as magnesium silicate or aluminum silicate. They behave substantially inertly with regard to the propylene partial oxidation. The support bodies can have a regular or irregular shape, although preference is given to regularly shaped support bodies having distinct surface roughness, for example spheres or hollow cylinders. It is suitable in accordance with the invention to use substantially nonporous, surface-roughened spherical supports made of steatite whose diameter is from 1 to 10 mm or to 8 mm, preferably from 4 to 5 mm. However, also relevant in accordance with the invention is the use of cylinders as support bodies, whose length is from 2 to 10 mm and whose external diameter is from 4 to 10 mm. In the case of rings as support bodies, the wall thickness is also typically from 1 to 4 mm. Annular support bodies to be used in accordance with the invention have a length of from 2 to 6 mm, an external diameter of from 4 to 8 mm and a wall thickness of from 1 to 2 mm. Support bodies suitable in accordance with the invention are also rings of geometry 7 mm×3 mm×4 mm (external diameter×length×internal diameter). The fineness of the catalytically active oxide compositions to be applied to the surface of the support body is of course adjusted to the desired coating thickness (cf. EP-A 714 700).

Multimetal oxide active compositions suitable in accordance with the invention for the step from propylene to acrolein are also compositions of the general formula V

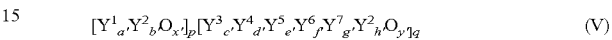

(V)

in which the variables are each defined as follows:
$Y^1$=only bismuth or bismuth and at least one of the elements tellurium, antimony, tin and copper,
$Y^2$=molybdenum, or tungsten, or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from >0 to 20,
f'=from 0 to 6,
g'=from 0 to 15,
h'=from 8 to 16,
x', y'=numbers which are determined by the valency and frequency of the elements in V other than oxygen and
p,q=numbers whose p/q ratio is from 0.1 to 10, comprising three-dimensional regions of the chemical composition $Y^1_{a'}Y^2_{b'}O_{x'}$ which are delimited from their local environment owing to their different composition from their local environment, and whose maximum diameter (longest direct line passing through the center of the region and connecting two points on the surface (interface) of the region) is from 1 nm to 100 µm, frequently from 10 nm to 500 nm or from 1 µm to 50 or 25 µm.

Particularly suitable multimetal oxide compositions V in accordance with the invention are those in which $Y^1$ is only bismuth.

Among these, preference is given in turn to those of the general formula VI

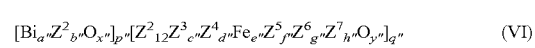

(VI)

in which the variables are each defined as follows:
$Z^2$=molybdenum, or tungsten, or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a''=from 0.1 to 1, b″=from 0.2 to 2,
c″=from 3 to 10,
d″=from 0.02 to 2,
e″=from 0.01 to 5, preferably from 0.1 to 3,
f″=from 0 to 5,
g″ from 0 to 10,
h″ from 0 to 1,
x″,y″=numbers which are determined by the valency and frequency of the elements in VI other than oxygen,
p″,q″=numbers whose p″/q″ ratio is from 0.1 to 5, preferably from 0.5 to 2, and very particular preference is given to those compositions VI in which $Z^2{}_{b''}=(\text{tungsten})_{b''}$ and $Z^2{}_{12}=(\text{molybdenum})_{12}$.

It is also of significance in accordance with the invention when at least 25 mol % (preferably at least 50 mol % and more preferably 100 mol %) of the total proportion of $[Y^1{}_aY^2{}_bO_x]_p$ ($[Bi_{a''}Z^2{}_{b''}O_{x''}]_{p''}$) of the multimetal oxide compositions V (multimetal oxide compositions VI) suitable in accordance with the invention in the multimetal oxide compositions V (multimetal oxide compositions VI) suitable in accordance with the invention is in the form of three-dimensional regions of the chemical composition $Y^1{}_aY^2{}_bO_{x'}$ $[Bi_{a''}Z^2{}_{b''}O_{x''}]$ which are delimited from their local environment owing to their different chemical composition from their local environment, and whose maximum diameter is in the range from 1 nm to 100 μm.

With regard to the shaping, the statements made for the multimetal oxide composition IV catalysts apply to multimetal oxide composition V catalysts.

The preparation of multimetal oxide active compositions V is described, for example, in EP-A 575 897 and also in DE-A 198 55 913.

The inert support materials recommended above are also useful, inter alia, as inert materials for the dilution and/or delimitation of the appropriate fixed catalyst beds, or as a preliminary bed which protects them and/or heats the reaction gas mixture fed.

For the second step (the second reaction stage), the heterogeneously catalyzed gas phase partial oxidation of acrolein to acrylic acid, useful active compositions for the catalysts required are, in accordance with the invention, in principle all multimetal oxide compositions comprising Mo and V, for example those of DE-A 100 46 928 and of DE-A 198 15 281.

A multitude thereof which are particularly favorable in accordance with the invention can be encompassed by the general formula VII

 (VII)

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in VII other than oxygen.

Embodiments which are particularly favorable in accordance with the invention among the active multimetal oxides VII are those which are encompassed by the following definitions of the variables of the general formula VII:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements in VII other than oxygen.

However, multimetal oxides VII which are very particularly favorable in accordance with the invention are those of the general formula VIII

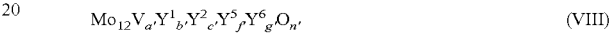 (VIII)

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements in VIII other than oxygen.

The multimetal oxide active compositions (VII) which are suitable in accordance with the invention are obtainable in a manner known per se, for example disclosed in DE-A 43 35 973 or in EP-A 714 700.

Generally, multimetal oxide active compositions suitable in accordance with the invention for the "acrolein→acrylic acid" step, especially those of the general formula VII, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions VII include those compounds which are already oxides and/or those compounds which can be converted to oxides by heating, at least in the presence of oxygen.

The starting compounds for the preparation of multimetal oxide compositions VII can be intimately mixed in dry or in wet form. When they are mixed in dry form, the starting compounds are appropriately used in the form of finely divided powder and subjected to calcining after mixing and, if appropriate, compaction. However, preference is given to intimate mixing in wet form.

This is typically done by mixing the starting compounds with one another in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, especially those of the general formula VII, may be used for an inventive partial acrolein oxidation either in powder form or shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of favorable unsupported catalyst geometries are solid cylinders or hollow cylinders having an external diameter and a length of from 2 to 10 mm. In the case of the hollow cylinders, a wall thickness of from 1 to 3 mm is appropriate. The unsupported catalyst may of course also have spherical geometry, in which case the spherical diameter may be from 2 to 10 mm (e.g. 8.2 mm or 5.1 mm).

The pulverulent active composition or its pulverulent precursor composition which is yet to be calcined can of course also be shaped by applying to preshaped inert catalyst supports. The coating of the support bodies to prepare the coated catalysts is generally performed in a suitable rotatable vessel, as disclosed, for example, by DE-A 2 909 671, EP-A 293 859 or by EP-A 714 700.

To coat the support bodies, the powder composition to be applied is appropriately moistened and is dried again after application, for example by means of hot air. The coating thickness of the powder composition applied to the support body is, in a manner relevant in accordance with the invention, frequently selected within the range from 10 to 1000 μm, preferably within the range from 50 to 500 μm and more preferably within the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders with grit layer. Suitable support bodies include substantially nonporous, surface-roughened, spherical supports made of steatite, whose diameter is from 1 to 10 mm or to 8 mm, preferably from 4 to 5 mm. In other words, suitable spherical geometries may have diameters of 8.2 mm or 5.1 mm. However, suitable support bodies also include cylinders whose length is from 2 to 10 mm and whose external diameter is from 4 to 10 mm. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Suitable support bodies are also in particular rings of geometry 7 mm×3 mm×4 mm (external diameter×length× internal diameter). The fineness of the catalytically active oxide compositions to be applied to the surface of the support body is of course adapted to the desired coating thickness (cf. EP-A 714 700).

Multimetal oxide active compositions suitable for the "acrolein→acrylic acid" partial oxidation step are also compositions of the general formula IX $$[D]_p[E]_q \quad (IX)$$

in which the variables are each defined as follows:
$D = Mo_{12}V_{a''}Z^1_{b''}Z^2_{c''}Z^3_{d''}Z^4_{e''}Z^5_{f''}Z^6_{g''}O_{x''}$,
$E = Z^7_{12}Cu_{h''}H_{i''}O_{y''}$,
$Z^1$=W, Nb, Ta, Cr and/or Ce,
$Z^2$=Cu, Ni, Co, Fe, Mn and/or Zn,
$Z^3$=Sb and/or $B^1$,
$Z^4$=Li, Na, K, Rb, Cs and/or H,
$Z^5$=Mg, Ca, Sr and/or Ba,
$Z^6$=Si, Al, Ti and/or Zr,
$Z^7$=Mo, W, V, Nb and/or Ta, preferably Mo and/or W,
a''=from 1 to 8,
b''=from 0.2 to 5,
c''=from 0 to 23,
d''=from 0 to 50,
e''=from 0 to 2,
f''=from 0 to 5,
g''=from 0 to 50,
h''=from 4 to 30,
i'', =from 0 to 20 and
x'',y''=numbers which are determined by the valency and frequency of the elements in IX other than oxygen and
p,q=numbers other than zero whose p/q ratio is from 160:1 to 1:1, and which are obtainable by separately preforming a multimetal oxide composition E

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the abovementioned elements in the stoichiometry D

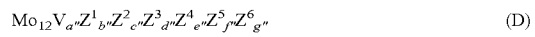

(starting composition 2) in the desired p:q ratio, drying the aqueous mixture which may result, and calcining the resulting dry precursor composition before or after drying at temperatures of from 250 to 600° C. to give the desired catalyst geometry.

Particularly suitable are the multimetal oxide compositions IX in which the preformed solid starting composition 1 is incorporated into an aqueous starting composition 2 at a temperature of <70° C. A detailed description of the preparation of multimetal oxide composition VI catalysts is contained, for example, in EP-A 668 104, DE-A 197 36 105, DE-A 100 46 928, DE-A 197 40 493 and DE-A 195 28 646.

With regard to the shaping, the statements made with regard to multimetal oxide composition IX catalysts apply. Multimetal oxide catalysts which are outstandingly suitable in accordance with the invention for the "acrolein→acrylic acid" step are also those of DE-A 198 15 281, especially having multimetal oxide active compositions of the general formula I of DE-A 198 15 281.

Advantageously, unsupported catalyst rings are used for the step from propylene to acrolein and coated catalyst rings for the step from acrolein to acrylic acid.

The fixed catalyst bed temperature for the first reaction stage (propylene→acrolein) is appropriately from 270 to 450° C., or from 280 to 420° C., preferably from 300 to 380° C. The fixed catalyst bed temperature for the second reaction stage (acrolein→acrylic acid) is appropriately from 200 to 370° C., or from 200 to 320° C., preferably from 220 to 380° C. When the process according to the invention is performed in one-zone multiple catalyst tube fixed bed reactors, the aforementioned temperatures correspond to the entrance temperature of the heat carrier (of the salt melt) into the vessel surrounding the catalyst tubes.

In principle, in the process according to the invention, the volume-specific activity in flow direction of the reaction gas mixture may be constant over the length of the flow path (i.e. over the length of the fixed catalyst bed) within the fixed catalyst bed for the first reaction stage freshly installed into the reaction chamber, or advantageously increase at least once (continuously or abruptly or in stages). In all aforementioned cases, it is also advantageous when the active composition does not change over the length of the flow path (i.e. within the fixed catalyst bed). The statements made above for the first reaction stage apply equally to the second reaction stage of a heterogeneously catalyzed fixed bed gas phase partial oxidation of propylene to acrylic acid.

To prepare the fixed catalyst bed installed freshly into the reaction chamber for the first reaction stage, it is possible to use only shaped catalyst bodies having multimetal oxide active composition or else substantially homogeneous mixtures of shaped catalyst bodies having multimetal oxide active composition and shaped bodies (shaped diluent bodies) which have no multimetal oxide active composition and behave substantially inertly with respect to the heterogeneously catalyzed partial gas phase oxidation. Useful materials for such inert shaped bodies are in principle all of those which are also suitable as support material for coated catalysts suitable in accordance with the invention. Useful such materials include, for example, porous or nonporous aluminum oxides, silicon dioxide, thorium dioxide, zirconium dioxide, silicon carbide, silicates such as magnesium silicate or aluminum silicate, or the steatite already mentioned.

The geometry of such inert shaped diluent bodies may in principle be as desired. In other words, they may be, for example, spheres, polygons, solid cylinders or else, like the shaped catalyst bodies having active composition, rings. Preferably in accordance with the invention, the inert shaped diluent bodies selected will be those whose geometry corresponds substantially to that of the shaped catalyst bodies to be diluted with them (the above statements also apply to substantially homogeneous mixtures of shaped catalyst bodies having multimetal oxide active composition and shaped diluent bodies usable for the provision of the fixed catalyst bed for the second reaction stage).

It is advantageous when the chemical composition of the active composition used does not change over the fixed catalyst bed for the first reaction stage installed freshly into the reaction chamber (fixed catalyst charge 1). In other words, the active composition used for an individual shaped catalyst body may be a mixture of different multimetal oxides, but the same mixture then preferably has to be used for all shaped catalyst bodies of the fixed catalyst charge 1.

The volume-specific (i.e. normalized to the unit of volume) activity can, as already stated, be reduced in a simple manner by homogeneously diluting a basic amount of shaped catalyst bodies produced in a uniform manner with shaped diluent bodies. The higher the fraction of the shaped diluent bodies selected, the lower the amount of active composition, or catalyst activity, present in a certain volume of the bed.

A volume-specific activity increasing at least once in flow direction of the reaction gas mixture over fixed bed catalyst charge 1 can thus be attained for the process according to the invention in a simple manner, for example, by beginning the bed with a high fraction of inert shaped diluent bodies based on one type of shaped catalyst bodies, and then reducing this fraction of shaped diluent bodies in flow direction either continuously or, at least once or more than once, abruptly (for example in stages). When the content of shaped diluent bodies is left constant or no shaped diluent bodies at all are used additionally in fixed bed catalyst charge 1, the result is a constant volume-specific activity in flow direction of the reaction gas mixture over fixed bed catalyst charge 1. However, an increase in the volume-specific activity is also possible, for example, by, with constant geometry and active composition type of a shaped coated catalyst body, increasing the thickness of the active composition layer applied to the support, or, in a mixture of coated catalysts with the same geometry but with different proportion by weight of the active composition, increasing the proportion of shaped catalyst bodies with higher proportion by weight of active composition. A similar effect can also be achieved, for example, by, in mixtures of unsupported catalysts and of coated catalysts (with identical active composition), altering the mixing ratio in an appropriate manner. It will be appreciated that the variants described can also be employed in combination.

Normally, in an inventive two-stage partial oxidation of propylene to acrylic acid, the volume-specific activity will decrease once neither within fixed bed catalyst charge 1 nor within fixed bed catalyst charge 2 (this is the fixed catalyst bed for the second reaction stage installed freshly into the reaction chamber) in flow direction of the reaction gas mixture.

Upstream and/or downstream of fixed bed catalyst charge 1 may be disposed beds consisting exclusively of inert material (for example only shaped diluent bodies) (for terminology purposes, they are not included in the fixed bed catalyst charge 1 in this document, since they do not comprise any shaped bodies which have multimetal oxide active composition). The shaped diluent bodies used for the inert bed may have the same geometry as the shaped catalyst bodies used in fixed bed catalyst charge 1. However, the geometry of the shaped diluent bodies used for the inert bed may also be different from the aforementioned geometry of the shaped catalyst bodies (for example, spherical instead of annular).

Preferably in accordance with the invention, fixed bed catalyst charge 1 in the process according to the invention is structured in flow direction of the reaction gas mixture as follows.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), in each case of the total length of fixed bed catalyst charge 1, either only shaped catalyst bodies or one homogeneous mixture (or two successive homogeneous mixtures with decreasing dilution) of shaped catalyst bodies and shaped diluent bodies (both preferably having substantially the same geometry), in which the proportion by weight of shaped diluent bodies (the mass densities of shaped catalyst bodies and of shaped diluent bodies generally differ only slightly) is normally from 5 to 40% by weight, or from 10 to 40% by weight or from 20 to 40% by weight or from 25 to 35% by weight. Downstream of this first zone of the fixed bed catalyst charge 1 is then disposed, advantageously in accordance with the invention, up to the end of the length of the section of fixed bed catalyst charge 1 (i.e., for example, to a length of from 2.00 to 3.50 m, preferably from 2.50 to 3.00 m), either a bed of shaped catalyst bodies diluted only to a lesser extent (than in the first zone), or, most preferably, a sole (undiluted) bed of the same shaped catalyst bodies which have also been used in the first zone.

The aforementioned is especially true when the shaped catalyst bodies used in fixed bed catalyst charge 1 are unsupported catalyst rings or coated catalyst rings (especially those which are mentioned in this document as preferred). For the purposes of the aforementioned structuring, both the shaped catalyst bodies and the shaped diluent bodies in the process according to the invention advantageously have substantially the ring geometry 5 mm×3 mm×2 mm (external diameter× length×internal diameter).

In a manner corresponding to that in which the volume-specific activity of fixed bed catalyst charge 1 can be varied, it is also possible to vary the volume-specific activity of fixed bed catalyst charge 2. Upstream and/or downstream of the actual fixed bed catalyst charge 2 may in turn be disposed an appropriate inert bed (for terminology purposes, it is not included in the fixed bed catalyst charge 2 in this document, since they do not comprise any shaped bodies which have multimetal oxide active composition).

Preferably in accordance with the invention, fixed bed catalyst charge 2 in the process according to the invention is structured as follows in flow direction of the reaction gas mixture.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), in each case of the total length of fixed bed catalyst charge 2, either only shaped catalyst bodies or one homogeneous mixture (or two successive homogeneous mixtures with decreasing dilution) of shaped catalyst bodies and shaped diluent bodies (both preferably having substantially the same geometry), in which the proportion by weight of shaped diluent bodies (the mass densities of shaped catalyst bodies and of shaped diluent bodies generally differ only slightly) is normally from 10 to 50% by weight, preferably from 20 to 45% by weight and more preferably from 25 to 35% by weight. Downstream of this first zone of fixed bed catalyst charge 2 is then disposed, advantageously in accordance with the invention, up to the end of the length of the section of fixed bed catalyst charge 2 (i.e., for example, to a length of from 2.00 to 3.50 m, preferably from 2.50 to 3.00 m), either a bed of shaped catalyst bodies diluted only to a lesser extent (than in the first zone), or, most preferably, a sole bed of the same shaped catalyst bodies which have also been used in the first zone.

The aforementioned is especially true when the shaped catalyst bodies used in fixed bed catalyst charge 2 are coated catalyst rings (especially those which are mentioned in this document as preferred). For the purposes of the aforementioned structuring, both the shaped catalyst bodies or their support rings and the shaped diluent bodies in the process according to the invention advantageously have substantially the ring geometry 7 mm×3 mm×4 mm (external diameter× length×internal diameter).

Generally, the fixed catalyst bed installed freshly into the reaction chamber and the remaining boundary conditions for both reaction stages will be configured such that, as described in EP-A 990 636 and in EP-A 1 106 598, both the hotspot formation and its thermal sensitivity are minimized ($\Delta T^{HB}$ is generally $\leq 80°$ C., usually $\leq 70°$ C., frequently from 20 to 70° C.; $\Delta T^{HB}$ is preferably low; the peak-to-salt temperature sensitivity is usually $\leq 9°$ C., or $\leq 7°$ C., or $\leq 5°$ C., or $\leq 3°$ C.)

It will be appreciated that, prior to an inventive partial fixed catalyst bed change, it is possible to employ all procedures mentioned in the prior art, each alone or in combination, which are suitable for delaying the requirement of an inventive partial change.

Appropriately from an application point of view, both the first and the second reaction stage will be carried out (operated) in a one-zone multiple catalyst tube fixed bed reactor already described as suitable for this purpose in this document with the fixed catalyst beds which have been described above as suitable and are each to be installed freshly into the reaction chamber. One-zone multiple catalyst tube fixed bed reactors suitable with preference in this regard are described by EP-A 700 714 and EP-A 700 893. In principle, it is also possible to employ a multizone multiple catalyst tube fixed bed reactor operating mode for both reaction stages, as described, for example, in DE-A 103 13 213, DE-A 10 2005 062 026, WO 2004/009525 and in DE-A 103 51 269.

Both in the first and in the second reaction stage, the working pressure may be either below standard pressure (for example up to 0.5 bar; the reaction gas mixture is sucked through the fixed catalyst bed) or above standard pressure. Typically, the working pressure in both reaction stages will be at values of from 1 to 5 bar, frequently from 1.5 to 3.5 bar. Normally, the working pressure in the two reaction stages will not exceed 100 bar.

The propylene loading of fixed bed catalyst charge 1 may be $\geq 80$ l(STP)/l·h, or $\geq 100$ l(STP)/l·h, or $\geq 120$ l(STP)/l·h, or $\geq 140$ l(STP)/l·h, or $\geq 165$ l(STP)/l·h, or $\geq 170$ l(STP)/l·h, or $\geq 175$ l(STP)/l·h, or $\geq 180$ l(STP)/l·h, or $\geq 185$ l(STP)/l·h, or $\geq 190$ l(STP)/l·h, or $\geq 200$ l(STP)/l·h, or $\geq 210$ l(STP)/l·h, or $\geq 220$ l(STP)/l·h, or $\geq 230$ l(STP)/l·h, or $\geq 240$ l(STP)/l·h, or $\geq 250$ l(STP)/l·h. Normally, the propylene loading of fixed bed catalyst charge 1 will not exceed 600 l(STP)/l·h. Typically, the propylene loadings of fixed bed catalyst charge 1 will be at values of $\leq 300$ l(STP)/l·h, frequently at values of $\leq 250$ l(STP)/l·h.

The total space velocity in the two reaction stages may, for example, be from 1000 to 3000 l(STP)/l·h. The aforementioned applies in the same way to the acrolein loading of fixed bed catalyst charge 2.

Useful sources for the molecular oxygen required in both reaction stages are both air and air depleted in molecular nitrogen, or pure molecular oxygen. In the reaction gas mixture for the first reaction stage, the molar $O_2$:propylene ratio will generally be $\geq 1$. In the reaction gas mixture for the second stage, the molar $O_2$:acrolein ratio will generally be $\geq 0.5$. In both stages, the molar ratio is typically $\leq 3$.

The reaction gas mixture with which fixed bed catalyst charge 1 is charged (also referred to in this document as reaction gas mixture 1) will generally have the following constituent volume (in l(STP)/l·h) ratios: propylene:oxygen: inert gases (including steam)=1:(1.0 to 3.0):(5 to 25), preferably 1:(1.7 to 2.3):(10 to 15).

The reaction gas mixture with which fixed bed catalyst charge 2 is charged (also referred to in this document as reaction gas mixture 2) will generally have the following constituent volume (in l(STP)/l·h) ratios: acrolein:oxygen: steam:inert gases (excluding steam)=1:(0.5 to 3):(0 to 20):(3 to 30), preferably 1:(1 to 3):(0.5 to 10):(7 to 18).

In principle, both reaction stages may be operated independently of one another. Frequently, however, the product gas mixture of the first stage is used to charge the second reaction stage. It has been found to be appropriate to cool the product gas mixture leaving the first reaction stage before it enters the second reaction stage in order to suppress postcombustion of parts of the acrolein formed in the first reaction stage. For this purpose, an aftercooler is typically connected between the two reaction stages. In the simplest case, this may be an indirect tube bundle heat transfer. Between the two reaction stages, secondary gas (molecular oxygen and/or inert gas) may be metered in. Frequently, air is metered to the product gas mixture of the first reaction stage before it is used to charge the second reaction stage. Appropriately from an application point of view, the reaction gas mixture is fed to fixed bed catalyst charge 1 preheated to the temperature of the fixed catalyst bed for the first reaction stage.

In the aforementioned aftercooler, the product gas mixture of the first reaction stage is generally cooled to a temperature of from 210 to 290° C., frequently from 230 to 280° C., or from 250 to 270° C. The cooling can quite possibly be effected to temperatures which are below the temperature of the fixed catalyst bed of the second reaction stage. It is favorable when both the product gas mixture of the first reaction stage and that of the second reaction stage still comprise up to 5% by volume, frequently up to 3% by volume, of excess molecular oxygen.

However, the aftercooling described is in no way obligatory and can generally be dispensed with especially when the path of the product gas mixture from the first reaction stage into the second reaction stage is kept short. Equally, an addition of secondary gas between the two reaction stages is not obligatory. It will normally be dispensed with especially when two one-zone multiple catalyst tube fixed bed reactors for the two reaction stages are combined to give what is then a two-zone multiple catalyst tube fixed bed reactor (also known as single reactor), as described, for example, in DE-C 28 30 765, in EP-A 911 313 and in EP-A 383 224. In this case, the first reaction stage will be realized in the first temperature zone and the second reaction stage in the second temperature zone of a two-zone multiple catalyst tube fixed bed reactor, and the reaction gas mixture for the first reaction stage comprises the added entire molecular oxygen requirement. The heat carriers of the two zones are generally separated substantially from one another by an appropriate separating metal sheet. In the cases of combination, the length of the reaction tubes in many cases corresponds to the lengths in corresponding uncombined tube bundle reactors.

In general, the first reaction stage is operated in such a way that the propylene conversion $C^P$ in single pass of the reaction gas mixture is $\geq 90$ mol % and the selectivity of acrolein formation and of acrylic acid by-product formation (based on propylene converted) taken together ($S^{AC}$) is $\geq 80$ mol %. Preferably, $C^P$ is $\geq 93$ mol %; $S^{AC}$ is advantageously $\geq 85$ mol %, or $\geq 90$ mol %, or $\geq 95$ mol %.

In a corresponding manner, the second reaction stage is generally operated in such a way that the acrolein conversion $C^A$ in single pass of the reaction gas mixture is $\geq 90$ mol %, often $\geq 93$ mol %, in many cases $\geq 95$ mol %, or $\geq 97$ mol %, or 99 mol %.

The selectivity of acrylic acid formation (based on acrolein converted) will regularly be $\geq 90$ mol %, often $\geq 93$ mol % and usually $\geq 96$ mol %.

It is favorable to operate the first reaction stage in such a way that the propylene content in the product gas mixture of this stage does not exceed the value of 10000 ppm by weight, preferably 6000 ppm by weight and more preferably 4000 or 2000 ppm by weight.

It is favorable to operate the second reaction stage in such a way that the acrolein content in the product gas mixture of this stage does not exceed the value of 1500 ppm by weight, preferably 600 ppm by weight and more preferably 350 ppm by weight.

In general, the reaction gas mixture for the first reaction stage (also known here as starting reaction gas mixture 1) in the process according to the invention comprises from 3 to 25% by volume, in many cases from 5 to 20% by volume and usually from 6 to 13% by volume of propylene.

Reaction gas mixture 2 generally comprises corresponding acrolein contents for feeding to the second reaction stage.

According to the invention, the content of molecular oxygen in starting reaction gas mixture 1 is normally such (as already mentioned) that the molar ratio $V_1$ of $O_2$ present in starting reaction gas mixture 1 to $C_3H_6$ present in starting reaction gas mixture 1 is $\geq 1$. Typically, $V_1$ in the process according to the invention is $\geq 1$ and $\leq 3$, usually $\geq 1.3$ and $\leq 2.5$, often from $\geq 1.5$ to $\leq 2.3$. The amount of molecular oxygen in starting reaction gas mixture 2 (the reaction gas mixture with which the fixed catalyst bed of the second reaction stage is charged), is, as already mentioned, normally such that the molar ratio of $O_2$ present in starting reaction gas mixture 2 to acrolein present in starting reaction gas mixture 2 is from $\geq 0.5$ to $\leq 3$, or $\leq 2$, frequently from $\geq 0.75$ to $\leq 1.5$.

It is also possible for starting reaction gas mixture 1 to comprise $\geq 0.01$, or $\geq 0.1$, or $\geq 0.5$, or $\geq 2\%$ by volume of $CO_2$. Usually, the aforementioned $CO_2$ content may be $\leq 25\%$ by volume.

Especially when the source used for the molecular oxygen in the process according to the invention is air, starting reaction gas mixture 1 will comprise molecular nitrogen as a further inert diluent gas. In principle, starting reaction gas mixture 1 in the process according to the invention may comprise $\geq 1\%$ by volume, or $\geq 5\%$ by volume, or $\geq 10\%$ by volume, or $\geq 20\%$ by volume, or $\geq 30\%$ by volume, or $\geq 40\%$ by volume of molecular nitrogen. However, the content in starting reaction gas mixture 1 of molecular nitrogen will generally be at values of $\leq 80$ mol %, or $\leq 70$ mol %, or $\leq 60$ mol %.

Starting reaction gas mixture 1 may also comprise propane as an inert diluent gas. This propane content of starting reaction gas mixture 1 may be up to 70% by volume (for example from 5 to 70% by volume), or up to 60% by volume, or to 50% by volume, or up to 40% by volume, or to 30% by volume, or to 20% by volume, or up to 10% by volume. Frequently, this propane content will be $\geq 0.5$ or $\geq 1\%$ by volume. However, it may also be at values of $\geq 0.01\%$ by volume, or $\geq 0.02\%$ by volume, or $\geq 0.03\%$ by volume. In general, starting reaction gas mixture 1 comprises $\leq 10\%$ by volume, in many cases $\leq 5\%$ by volume of propane.

In the process according to the invention, this propane may be added, for example, deliberately as an inert diluent gas to be supplied separately to starting reaction gas mixture 1.

However, it will be appreciated that the propane may also be part of starting reaction gas mixture 1 by virtue of a partial dehydrogenation or oxydehydrogenation of propane functioning as the propylene source therefor (generally, these are effected under heterogeneous catalysis). In other words, the propylene present in starting reaction gas mixture 1 may be supplied to starting reaction gas mixture 1 at least partly with accompaniment by unconverted propane from a partial dehydrogenation (for example homogeneously and/or heterogeneously catalyzed, in the presence and/or with exclusion of molecular oxygen).

The process according to the invention comprises in particular also those embodiments in which starting reaction gas mixture 1 comprises from >0 to 35% by volume, frequently from 1 to 25% by volume, or from 5 to 15% by volume, or to 10% by volume of $H_2O$.

Typical starting reaction gas mixtures 1 are, for example, those which comprise:
  from 5 or 6 to 11% by volume of propene,
  from 2 or 6 to 12% by volume of water,
  from $\geq 0$, frequently $\geq 0.5$ or $\geq 1$ to 10% by volume of propane,
  from $\geq 0$ to 5% by volume of constituents other than propene, propane, water, oxygen and nitrogen,
  sufficient molecular oxygen that $V_1$ is from 1 to 3, and, as the remainder up to 100% by volume of the total amount, molecular nitrogen.

Inventive starting reaction gas mixtures 1 may also comprise:
from 6 to 9% by volume of propylene,
from 8 to 18% by volume of molecular oxygen,
from 6 to 30 or to 35% by volume of propane and
from 32 to 72% by volume of molecular nitrogen.

Inventive starting reaction gas mixtures 2 may, for example, comprise:
from 4.5 to 8% by volume of acrolein,
from 2.25 to 9% by volume of molecular oxygen,
from 6 to 30 or to 35% by volume of propane,
from 32 to 72% by volume of molecular nitrogen,
from 5 to 30% by volume of steam.

Inventive starting reaction gas mixtures 1 may also comprise up to 20% by volume of $H_2$.

In other words, starting reaction gas mixtures 1 of the process according to the invention may also comprise:
from 4 to 25% by volume of propylene,
from 6 to 70% by volume of propane,
from 5 to 60% by volume of $H_2O$,
from 8 to 65% by volume of $O_2$ and
from 0.3 to 20% by volume of $H_2$.

However, the process according to the invention is also favorable when starting reaction gas mixture 1 comprises from 0.1 to 30% by volume of $CO_2$.

Starting reaction gas mixtures 2 possible in accordance with the invention may also comprise:
from 3 to 25% by volume of acrolein,
from 5 to 65% by volume of molecular oxygen,
from 6 to 70% by volume of propane,
from 0.3 to 20% by volume of molecular hydrogen and
from 8 to 65% by volume of steam.

It is essential to the invention that, for all aforementioned cases, the process according to the invention can be employed for both stages in each case both when the two stages are operated independently of one another and when they are operated in series connection as detailed above. However, it is also successful when both steps, as described in DE-A 101 21 592, are implemented in one reactor over one charge.

The partial fixed catalyst bed change (as is quite generally the case in the processes according to the invention of this document) may in all cases extend in flow direction (of the reaction gas mixture) to up to 80%, or only to up to 70%, or only to up to 60%, or only to up to 50%, or only to up to 40%, or only to up to 30%, or preferably to up to 25%, more preferably to from 30 to 50% and most preferably to from 35 to 45% of the bed length of the particular fixed catalyst bed (a top charge consisting of inert material to an extent of 100% (the first charge from the flow point of view) is not counted as belonging to the fixed catalyst bed; for reasons of convenience, this top charge was, though, also exchanged; in a corresponding manner, a final charge consisting of inert material to an extent of 100% (the end charge from the flow point of view) was not counted as belonging to the fixed catalyst bed; however, an intermediate charge consisting of inert material to an extent of 100% was counted as belonging to the fixed catalyst bed). Appropriately, the aforementioned percentage for a partial catalyst change is frequently not less than 10 or 20%.

Finally, it should be mentioned once again that, in particular, a portion of charge gas mixture of the first stage ("propylene→acrolein") may be cycle gas. This is gas which remains after the product removal (acrylic acid removal) from the product gas mixture of the second stage, and, in the case of a series connection of the two stages, is generally partly recycled as inert diluent gas to charge the first and/or second stage.

A typical cycle gas composition is:
0-0.1% by volume of others, for example diphenyl, diphenyl ether and/or dimethyl phthalate,
0-0.1% by volume of acrylic acid,
0-0.1% by volume of acrolein,
3-5% by volume of oxygen,
1-5% by volume of steam,
0-3% by volume of carbon monoxide,
0-8% by volume of carbon dioxide,
0-2% by volume of propane,
0.1-0.5% by volume of propylene,
85-95% by volume of nitrogen.

The acrylic acid removal may be removed, for example, as described in EP-A 982 287, EP-A 982 289, DE-A 199 24 532, DE-A 101 15 277, DE-A 196 06 877, DE-A 197 40 252, DE-A 196 27 847, DE-A 100 53 086, EP-A 982 288 and DE-A 196 27 847.

In principle, the partial fixed catalyst bed change can be carried out at any time, i.e., for example, after one year, two years, three years or more years of operating time. In general, it will be carried out in accordance with economic considerations.

Finally, it should be mentioned that the inventive partial fixed catalyst bed change generally also has an advantageous effect on the pressure drop as the reaction gas mixture passes through the catalyst charge.

It should also be mentioned once again that the heat exchange media (heat carriers, salt melts) are preferably conducted through the relevant multiple catalyst tube fixed bed reactors in such amounts that the difference between their inlet and their outlet temperature is $\leq 5°$ C.

EXAMPLE AND COMPARATIVE EXAMPLE

I. General Description of the First Reaction Stage

Heat carrier used: Salt melt of 60% by weight of potassium nitrate and 40% by weight of sodium nitrite is conducted in countercurrent to the reaction gas mixture. With a fresh charge of the catalyst tube with fixed catalyst bed, it was fed with a temperature of 320° C. and removed with a temperature of 322° C.

Material of the catalyst tube disposed in a multiple catalyst tube fixed bed reactor: ferritic steel Composition of the catalyst tube: length 3200 mm
internal diameter 26 mm
external diameter 31 mm
(wall thickness 2.5 mm)

Composition of starting reaction gas mixture 1: 5.4% by volume of propylene,
10.5% by volume of molecular oxygen,
1.2% by volume of COX,
81.3% by volume of $N_2$, and
1.6% by volume of $H_2O$.

Propylene loading of the catalyst charge: 110 l(STP)/l·h

Fresh charge of the catalyst tube (in flow direction of the reaction gas mixture) Zone A: 50 cm
Preliminary bed of steatite rings of geometry 7 mm×7 mm×4 mm (external diameter×length×internal diameter)
Zone B: 100 cm
Catalyst charge with a homogeneous mixture of 30% by weight of steatite rings (steatite C 220 from CeramTec) of geometry 5 mm×3 mm×2 mm (external diameter×length×internal diameter) and 70% by weight of unsupported catalyst from zone C.

Zone C: 170 cm

Catalyst charge with annular (5 mm×3 mm×2 mm=external diameter×length×internal diameter) unsupported catalyst according to Example 1 of DE-A 100 46 957

II. Intermediate Cooling and Secondary Gas Addition

The product gas mixture of the first reaction stage was cooled to 250° C. by indirect heat exchange with a salt melt of 60% by weight of potassium nitrate and 40% by weight of sodium nitrite in a tube bundle heat exchanger substantially without acrolein loss. Subsequently, compressed air having a temperature of 140° C. was added in such an amount that the molar ratio of $O_2$:acrolein in the resulting mixture was approx. 1.28. This mixture was fed to the second reaction stage with a temperature of 220° C.

III. General Description of the Second Reaction Stage

The catalyst tube corresponded to that in the first reaction stage. Salt melt (same composition as in the first reaction stage) and reaction gas mixture were conducted in countercurrent. With a fresh charge of the catalyst tube with fixed catalyst bed, the salt melt was fed with a temperature of 260° C. and removed with a temperature of 262° C.

The fresh charge of the catalyst tube was (in flow direction of the reaction gas mixture)

Zone A:

20 cm preliminary bed of steatite rings (Steatit C 220 from CeramTec) of geometry 7 mm×7 mm×4 mm (external diameter×length×internal diameter).

Zone B:

100 cm catalyst charge (alternatively: 120 cm) with a homogeneous mixture of 30 (alternatively: 35) % by weight of steatite rings (steatite C 220 from CeramTec) of geometry 7 mm×3 mm×4 mm (external diameter×length×internal diameter) and 70 (alternatively: 65) % by weight of coated catalyst from zone C.

Zone C:

200 (alternatively: 180) cm catalyst charge with annular (approx. 7 mm×3 mm×4 mm=external diameter× length×internal diameter) coated catalyst according to Preparation Example 5 of DE-A 100 46 928.

IV. Results (the Selectivity of Acrylic Acid Formation Remained Substantially Constant)

A) Example

The analysis of the product gas mixture of the second reaction stage gave the following results:

The conversion of the acrolein formed in the first reaction stage with fixed catalyst bed installed freshly into the second reaction stage (on completion of conditioning thereof), at an inlet temperature $T^{in}$ of the salt melt into the second stage of 260° C., was 99.3 mol % at a selectivity of acrylic acid formation of 88.9 mol % (just like the data below, these data are based on single pass).

With increasing operating time, the acrolein conversion in the second reaction stage fell. Gradual increase in the inlet temperature of the salt melt into the second reaction stage allowed this loss of activity to be balanced out (the deactivation rate was stable at 8° C./year).

As $T^{in}$ of 283° C. was attained, $\Delta T^{HB}_v$ was 33° C. The process was then interrupted and the entire zone A and the entire zone B in the second reaction stage were sucked out and replaced by a fresh zone A and a fresh zone B, except that the fresh zone B had only 50% by weight of the steatite rings of geometry 7 mm×3 mm×4 mm and only 50% by weight of fresh coated catalyst according to Preparation Example 5 of DE-A 100 46 928.

With a $T^{in}$ of 275° C., it was subsequently possible to continue the process otherwise unchanged at acrolein conversion 99.3 mol % with a deactivation rate of 12° C./year and a $\Delta T^{HB}_n$ of 32° C.

B) Comparative Example

The procedure of the example was repeated, except that the zone B sucked out was replaced by a fresh zone B which, like the original zone B, had only 30% by weight of the steatite rings of geometry 7 mm×3 mm×4 mm and 70% by weight of fresh coated catalyst according to Preparation Example 5 of DE-A 100 46 928.

Although it was subsequently possible to continue the process with an acrolein conversion of 99.3 mol % at a $T^{in}$ of only 270° C., $\Delta T^{HB}_n$ was 48° C. and the deactivation rate was 20° C./year.

U.S. Provisional Patent Application No. 60/756,207, filed on Jan. 5, 2006, is incorporated into the present patent application by literature reference.

With respect to the aforementioned teachings, numerous changes to and deviations from the present invention are possible.

It can therefore be assumed that the invention, within the context of the attached claims, can be performed differently from the way specifically described herein.

What is claimed is:

1. A process for heterogeneously catalyzed gas phase partial oxidation of at least one organic starting compound comprising:

freshly installing into a reaction chamber, a bed of fixed catalyst;

conducting a reaction gas mixture comprising the at least one organic starting compound and molecular oxygen through the bed of fixed catalyst;

removing heat of reaction by indirect heat exchange with a fluid heat carrier conducted outside the reaction chamber;

replacing a portion of the fixed catalyst bed by a replacement fixed catalyst bed part;

wherein the replacing a portion of the fixed catalyst bed takes place when with increasing operating time the activity of the fixed catalyst bed is reduced, the portion of the fixed catalyst bed replaced is not the entire fixed catalyst bed, and a volume-specific activity of the replacement fixed catalyst bed part is lower than a volume-specific activity of the replaced fixed catalyst bed part in its freshly installed state wherein $d\Delta T = \Delta T^{HB}_n - \Delta T^{HB}_v$, is $\leq 30°$ C.

wherein $\Delta T^{HB}_n$ is the hotspot expansion of the fixed catalyst bed after the replacement by the replacement fixed catalyst bed part has been carried out, $\Delta T^{HB}_v$ is the hotspot expansion of the fixed catalyst bed before the replacement by the replacement fixed catalyst bed part has been carried out, based on the same conversion of the organic starting compound in single pass of the reaction gas mixture through the fixed catalyst bed and the same composition of the reaction gas mixture and the same loading of the fixed catalyst bed with reaction gas mixture.

2. The process according to claim 1, wherein the heterogeneously catalyzed gas phase partial oxidation is at least one selected from the group consisting of propylene to acrolein and/or acrylic acid, isobutene to methacrolein and/or methacrylic acid, acrolein to acrylic acid, methacrolein to methacrylic acid, propane to acrylic and, isobutane to methacrylic acid.

3. The process according to claim 1, wherein the at least one organic starting compound is at least one organic starting compound from the group consisting of propylene, acrolein, 1-butene, 2-butene, ethane, benzene, m-xylene, p-xylene, isobutane, isobutene, tert-butanol, isobutyraldehyde, methyl ether of tert-butanol, o-xylene, naphthalene, butadiene, ethylene, propane and methacrolein.

4. The process according to claim 1, wherein the gas phase partial oxidation is the second stage of a two-stage gas phase partial oxidation.

5. The process according to claim 4, wherein the gas phase partial oxidation is the partial oxidation of acrolein to acrylic acid in a two-stage gas phase partial oxidation of propylene to acrylic acid.

6. The process according to claim 1, wherein $d\Delta T$ is from $-15$ to $+10$ ° C.

7. The process according to claim 1, wherein $d\Delta T$ is from $-10$ to $0°$ C.

8. The process according to claim 1, wherein the reaction chamber is the interior of a reaction tube.

9. The process according to claim 8, wherein the reaction tube is disposed in a tube bundle reactor.

10. The process according to claim 1, wherein a part of the fixed catalyst bed replaced by the replacement fixed catalyst bed part extends in flow direction of the reaction gas mixture to up to 80% of a bed length of the fixed catalyst bed.

* * * * *